(12) United States Patent
Boyd

(10) Patent No.: US 9,994,589 B2
(45) Date of Patent: Jun. 12, 2018

(54) COMPOUNDS AND METHODS FOR THE TREATMENT OF ALZHEIMER'S DISEASE AND/OR CEREBRAL AMYLOID ANGIOPATHY

(71) Applicant: Amicus Therapeutics, Inc., Cranbury, NJ (US)

(72) Inventor: Robert Boyd, Horsham, PA (US)

(73) Assignee: Amicus Therapeutics, Inc., Cranbury, NJ (US)

(*) Notice: Subject to any disclaimer, the term of this patent is extended or adjusted under 35 U.S.C. 154(b) by 0 days. days.

(21) Appl. No.: 15/377,437

(22) Filed: Dec. 13, 2016

(65) Prior Publication Data

US 2017/0166588 A1 Jun. 15, 2017

Related U.S. Application Data

(60) Provisional application No. 62/266,760, filed on Dec. 14, 2015.

(51) Int. Cl.
*C07D 513/04* (2006.01)
*C07D 211/56* (2006.01)

(52) U.S. Cl.
CPC .......... *C07D 513/04* (2013.01); *C07D 211/56* (2013.01)

(58) Field of Classification Search
CPC ............................ C07D 211/56; C07D 513/04
See application file for complete search history.

(56) References Cited

U.S. PATENT DOCUMENTS 9,522,883 B2 * 12/2016 McEachern .......... A61K 31/445

FOREIGN PATENT DOCUMENTS

| WO | 2010015816 A2 | 2/2010 |
| WO | 2011049787 A1 | 4/2011 |
| WO | 2014032187 A1 | 3/2014 |
| WO | WO2014/032187 A1 * | 3/2014 |
| WO | 2015160796 A1 | 10/2015 |

OTHER PUBLICATIONS

PCT International Search Report and Written Opinion in PCT/US2016/066572 dated Apr. 12, 2017, 18 pages.
De La Fuente, et al., "Stereoselective Synthesis of 2-Acetamido-1,2-dideoxyallonojirimycin (DAJNAc), a New Potent Hexosaminidase Inhibitor", Organic Letters 2013, vol. 15, No. 14, pp. 3638-3641.
De La Fuente, et al., "Stereoselective synthesis of 2-acetamido-1,2-dideoxynojirimycin (DNJNAc) and ureido-DNJNAc derivatives as new hexosaminidase inhibitorst", Org. Biomol. Chem. 2015, 13, 6500-6510.
Glawar, et al., "Scalable Syntheses of Both Enantiomers of DNJNAc and DGJNAc from Glucuronolactone: The Effect of N-Alkylation on Hexosaminidase Inhibition", Chem. Eur. J. 2012, vol. 18, No. 30, pp. 9341-9359.
Stubbs, et al., "The Development of Selective Inhibitors of NagZ: Increased Susceptibility of Gram-Negative Bacteria to USPTO β Lactams", ChemBioChem 2013, vol. 14, pp. 1973-1981.

* cited by examiner

*Primary Examiner* — Timothy R Rozof
(74) *Attorney, Agent, or Firm* — Servilla Whitney LLC

(57) ABSTRACT

Described herein are novel compounds and methods for the treatment and/or prevention of cerebral amyloidoses such as Alzheimer's disease (AD) and/or cerebral amyloid angiopathy (CAA).

13 Claims, No Drawings

COMPOUNDS AND METHODS FOR THE TREATMENT OF ALZHEIMER'S DISEASE AND/OR CEREBRAL AMYLOID ANGIOPATHY

CROSS-REFERENCE TO RELATED APPLICATIONS

This application claims the benefit under 35 U.S.C. § 119(e) to U.S. Provisional Application No. 62/266,760, filed Dec. 14, 2015, the entire contents of which are incorporated herein by reference in their entirety.

TECHNICAL FIELD

The present invention generally pertains to the treatment of human cerebral amyloidoses such as Alzheimer's disease and/or cerebral amyloid angiopathy.

BACKGROUND

Alzheimer's disease is one of the largest socioeconomic healthcare burdens. Alzheimer's disease is characterized by progressive dementia and histopathologically by the presence of neurofibrillary tangles (NFTs) and neuritic (senile) plaques. Plaques consist of a protein called amyloid-beta (Aβ) and tangles are made up of a protein called tau.

Amyloid plaques and NFTs are both hallmarks of Alzheimer's disease (AD). Mutations in amyloid precursor protein (APP) and presenilin lead to early onset forms of Alzheimer's disease, supporting the hypothesis that the processing of APP may also play an important role in the pathogenesis of sporadic AD. Furthermore, the "amyloid hypothesis" predicts that the accumulation of Aβ in some toxic form is harmful to the brain. APP can be processed by α- and β-secretase pathways. To date, most research efforts to develop AD therapies that retard the progression of the disease are focused on inhibition of γ-secretase and β-secretase and the metabolism of APP to form Aβ peptide or activation of α-secretase processing to increase production of the neuroprotective sAPPα peptide while reducing Aβ production. Developing specific β-secretase inhibitors has been difficult, in part because there appears to be a nonlinear relationship between decrease of β-secretase activity in vivo, and a reduction of Aβ peptides in the brain. A further difficulty is the low brain penetration of most inhibitors, γ-secretase inhibitors have been further plagued with severe GI side effects associated with notch inhibition since γ-secretase processes numerous other substrates in addition to APP, including the notch receptor. Additionally, a deficiency of γ-secretase activity has been shown to cause neurodegeneration and may be associated with autosomal-dominant early-onset Alzheimer's disease caused by mutations in presenilin 1 (a component of the γ-secretase complex that contains the active site of the γ-secretase complex).

The majority of efforts aimed at treating Alzheimer's disease have focused on reducing the symptoms of AD. In particular, identification of a lower concentration of choline acetyltransferase in affected neurons of the forebrains of AD patients has led to treatments aimed at inhibiting the hydrolysis of acetylcholine in the synaptic cleft and prolonging the level of acetylcholine at the synapse. Although this strategy has resulted in at least a partial correction of neurotransmitter levels, the therapeutic benefits have been small.

Further, AD is categorized as a tauopathy. Tauopathies are caused by abnormal hyperphosphorylation of tau promoting its aggregation and formation of NFTs. Since mutations in tau and APP both cause dementia, one or both may contribute to the disease progression of AD. It is well understood that mutations leading to altered processing of APP cause AD. Currently, there are no approved therapies for slowing the progression of Alzheimer's disease. Thus, there remains a need for more beneficial AD treatments. While most therapies in development are focused on altering APP metabolism (e.g. β-secretase and γ-secretase inhibition) or blocking tau aggregation, the present invention provides a treatment using pharmacological chaperones which bind to one or more gangliosidases and/or sialidases and thereby increase the production of sAPPα and reduce the production of Aβ and hyperphosphorylated tau.

Similarly, cerebral amyloid angiopathy (CAA) is a disorder characterized by amyloid deposition in the walls of blood vessels of the central nervous system, particularly in the leptomeningeal and cortical arteries. CAA occurs mostly as a sporadic condition in the elderly, and its incidence is associated with advancing age. These sporadic CAA cases are due to deposition of Aβ, originating from proteolytic cleavage of APP. Hereditary forms of CAA are generally familial, more severe and earlier in onset than sporadic CAA. CAA has also recently been recognized as a potential contributor to the development of AD.

SUMMARY

It has been found that pharmacological chaperones that target β-hexosaminidase (β-hex) can have many benefits, including use in the treatment and/or prevention of cerebral amyloidoses such as Alzheimer's disease (AD) and/or cerebral amyloid angiopathy (CAA). There is a need for novel compounds that are pharmacological chaperones for β-hex and/or may be used in the synthesis of compounds that are chaperones for β-hex.

Accordingly, one aspect of the present invention pertains to a compound having a structure represented by formula I or IA:

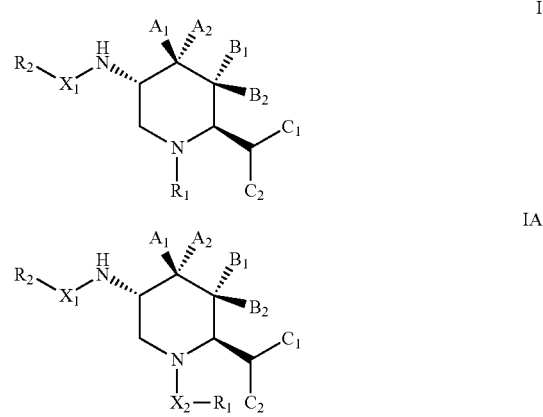

wherein: $R^1$, $R^2$, $R^4$ are independently chosen from H, $C_1$-$C_8$ alkyl, aryl, $(CH_2)_n$ aryl, $(CH_2)_n$ heteroaryl;
n=0-8;
$X^1$, $X^2$ are independently chosen from CO, SO, $SO_2$, —CONH—, $SO_2NH$—, SONH—; and
$A^1$, $A^2$, $B^1$, $B^2$, $C^1$, $C^2$ are independently chosen from H, $OR^4$, F,
with the proviso that the compound is not 2-acetamido-1,2-dideoxynojirimycin or 2-acetamido-1,2-dideoxygalactonojirimycin, or a pharmaceutically acceptable salt, solvate, or prodrug thereof.

In some embodiments, $R^4$ is H or benzyl. In particular embodiments, the compound is selected from the group consisting of:

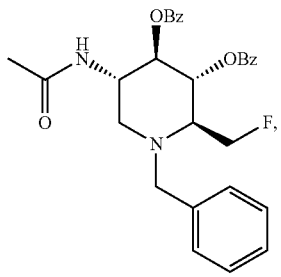

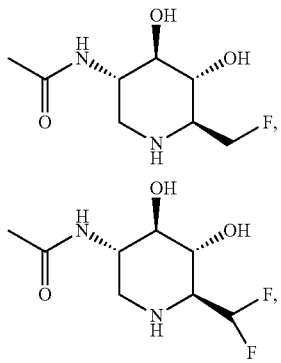

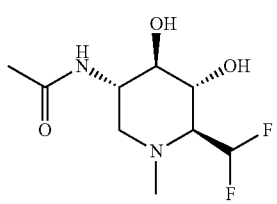

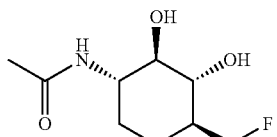

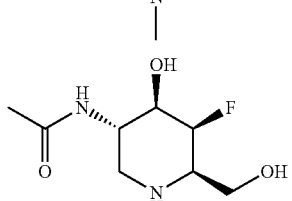

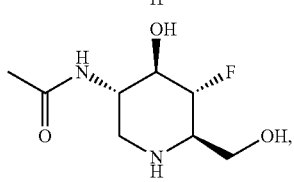

or a pharmaceutically acceptable salt, solvate, or prodrug thereof.

Another aspect of the present invention pertains to a compound having a structure represented by formula II or IIA:

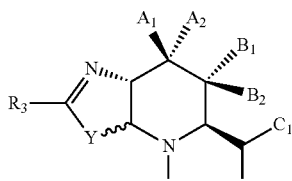

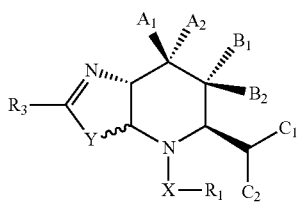

wherein: $R^1$, $R^3$, $R^4$ are independently chosen from H, $C_1$-$C_8$ alkyl, aryl, $(CH_2)_n$ aryl, $(CH_2)_n$ heteroaryl; n=0-8;
X=CO, SO, $SO_2$, —CONH—, $SO_2NH$—, SONH—;
Y=O, S, NH; and
$A^1$, $A^2$, $B^1$, $B^2$, $C^1$, $C^2$ are independently chosen from H, $OR^4$, F, or a pharmaceutically acceptable salt, solvate, or prodrug thereof.

In some embodiments, $R^4$ is H or benzyl. In particular embodiments, the compound has the following structure:

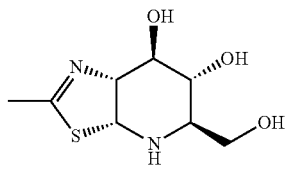

or a pharmaceutically acceptable salt, solvate, or prodrug thereof.

Another aspect of the present invention pertains to a compound having a structure represented by formula III:

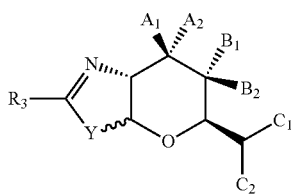

wherein: $R^3$, $R^4$ are independently chosen from H, $C_1$-$C_8$ alkyl, aryl, $(CH_2)_n$ aryl, $(CH_2)_n$ heteroaryl; n=0-8;
Y=O, S, NH; and
$A^1$, $A^2$, $B^1$, $B^2$, $C^1$, $C^2$ are independently chosen from H, $OR^4$, F, with the proviso that the compound is not N-acetyl-glucosaminethiazoline,
or a pharmaceutically acceptable salt, solvate, or prodrug thereof.

In some embodiments, $R^4$ is H or benzyl. In particular embodiments, the compound is selected from the group consisting of:

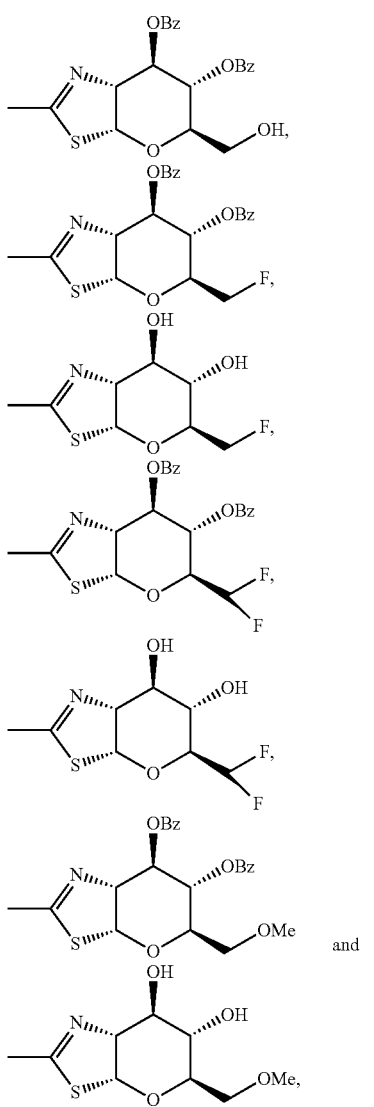

or a pharmaceutically acceptable salt, solvate, or prodrug thereof.

Another aspect of the present invention pertains to a pharmaceutical composition comprising a compound according to any of the above compounds; and at least one pharmaceutically acceptable carrier. In yet another aspect, the invention relates to a method of making the pharmaceutical composition. In one or more embodiments, the method comprises adding to at least one pharmaceutically acceptable carrier a compound having a structure represented by any of formulae I-III.

Yet another aspect of the present invention pertains to a method of preventing and/or treating cerebral amyloidoses such as Alzheimer's disease (AD) and/or cerebral amyloid angiopathy (CAA). In one or more embodiments, the method comprises administering to a patient in need thereof a therapeutically effective amount of a compound having a structure represented by any of formulae I-III. In some embodiments, the administration of an effective amount of the compound increases processing of one or more gangliosides selected from GM2 and GA2.

Another aspect of the present invention pertains to a method for enhancing the activity of β-hexosaminidase, the method comprising administering an effective amount of a compound having a structure represented by any of formulae I-III.

Yet another aspect of the present invention pertains to a kit comprising a compound having a structure represented by any of formulae I-III, and instructions for using the compound to treat and/or prevent Alzheimer's disease and/or cerebral amyloid angiopathy.

DETAILED DESCRIPTION

Definitions

The terms used in this specification generally have their ordinary meanings in the art, within the context of this invention and in the specific context where each term is used. Certain terms are discussed below, or elsewhere in the specification, to provide additional guidance to the practitioner in describing the invention and how to make and use the invention.

As used herein, the term "pharmacological chaperone," or sometimes "specific pharmacological chaperone" ("SPC"), refers to a molecule that specifically binds to a protein, particularly an enzyme, and has one or more of the following effects: (i) enhancing the formation of a stable molecular conformation of the protein (both wild-type and mutant proteins); (ii) enhances proper trafficking of the protein from the endoplasmic reticulum (ER) to another cellular location, preferably a native cellular location, i.e., preventing ER-associated degradation of the protein; (iii) preventing aggregation of conformationally unstable, i.e., misfolded proteins; (iv) restoring or enhancing at least partial wild-type function, stability, and/or activity of the protein; and/or (v) improving the phenotype or function of the cell harboring a mutant protein. Thus, a pharmacological chaperone is a molecule that specifically binds to a protein, resulting in proper folding, trafficking, non-aggregation, and/or activity of that protein. In the context of the present invention, the specific pharmacological chaperones are substrates, or substrate analogs or derivatives, of the enzymes.

The wild-type activity/amount can be increased in vivo and/or for co-formulation for ERT. The mutant can be stabilized/enhanced in vivo through the endoplasmic reticulum, etc. Both mutant and wild type proteins in the same patient can be stabilized if both are present (such as the case with X-linked diseases). Thus, one or more embodiments of the invention pertain to enhancement of the enzyme (recombinant or native/mutant) and different types of administration (co-formulation with recombinant, co-administration with recombinant, monotherapy for the mutant enzyme that is endogenously produced, and any combination of the above.)

As used herein, the term "substrate" refers to a molecule that is acted upon (i.e., modified) by an enzyme. According to the present invention, this term refers to an enzyme's natural or physiological substrate that is unmodified by human intervention.

The term "β-hexosaminidase" (β-Hex) includes all three isoforms of the enzyme, including β-hexosaminidase A, β-hexosaminidase B and β-hexosaminidase S. β-hexosaminidase catabolizes GM2 gangliosides and its deficiency causes the autosomal recessive lysosomal storage disorders Tay-Sachs disease and Sandhoff disease. β-hexosaminidase A is composed of an α-subunit and a β-subunit (αβ), β-hexosaminidase B is composed of two β-subunits (ββ) and β-hexosaminidase S is composed of two α-subunits (αα). The compounds and methods disclosed herein may act on only one isoform of the enzyme, two of the isoforms or all three of the isoforms.

The terms "therapeutically effective dose" and "effective amount" refer to the amount of the specific pharmacological chaperone that is sufficient to result in a therapeutic response. A therapeutic response may be any response that a user (e.g., a clinician) will recognize as an effective response to the therapy, including the foregoing symptoms and surrogate clinical markers. Thus, a therapeutic response will generally be an amelioration of one or more symptoms of a disease or disorder, e.g., a lysosomal storage disease, such as those known in the art for the disease or disorder, e.g., neurological symptoms.

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

As used herein, "aryl" refers to aromatic radicals having in the range of about 6 to about 14 carbon atoms such as phenyl, naphthyl, tetrahydronapthyl, indanyl, biphenyl. The term "arylalkyl" refers to an aryl group as defined above directly bonded to an alkyl group, e.g., —$CH_2C_6H_5$, and —$C_2H_4C_6H_5$.

Compounds

One aspect of the invention pertains to a compound having a structure represented by formula I or IA:

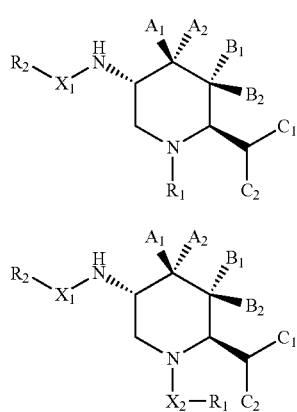

wherein: $R^1$, $R^2$, $R^4$ are independently chosen from H, $C_1$-$C_8$ alkyl, aryl, $(CH_2)_n$ aryl, $(CH_2)_n$ heteroaryl; n=0-8;

$X^1$, $X^2$ are independently chosen from CO, SO, $SO_2$, —CONH—, $SO_2NH$—, SONH—; and $A^1$, $A^2$, $B^1$, $B^2$, $C^1$, $C^2$ are independently chosen from H, $OR^4$, F.

In certain embodiments, the compound of formula I or IA is not 2-acetamido-1,2-dideoxynojirimycin (AdDNJ) and/or the compound is not 2-acetamido-1,2-dideoxygalactonojirimycin (AdDGJ).

Embodiments of the present invention also relate to pharmaceutically acceptable salts, solvates, or prodrugs of the compounds of formula I or IA.

In some embodiments, $R^4$ is H or benzyl. In particular embodiments, the compound is selected from the group consisting of:

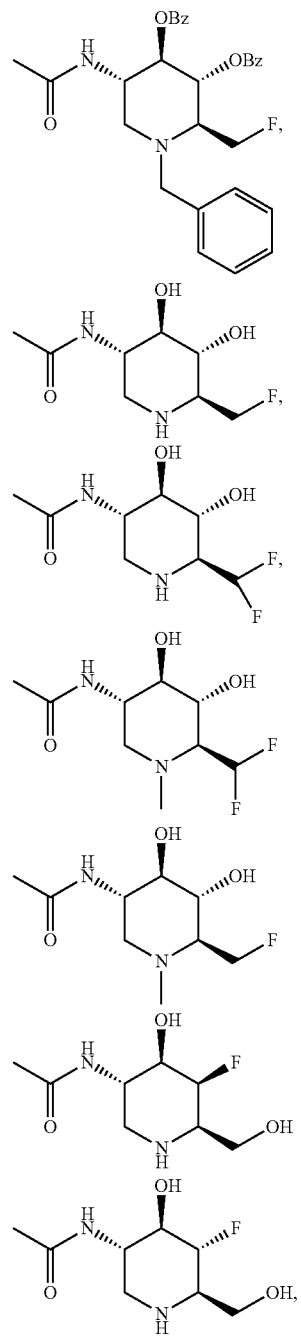

and or a pharmaceutically acceptable salt, solvate, or prodrug thereof.

Another aspect of the present invention pertains to a compound having a structure represented by formula II or IIA:

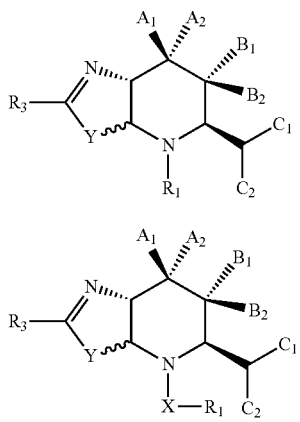

wherein: $R^1$, $R^3$, $R^4$ are independently chosen from H, $C_1$-$C_8$ alkyl, aryl, $(CH_2)_n$ aryl, $(CH_2)_n$ heteroaryl; n=0-8;
X=CO, SO, $SO_2$, —CONH—, $SO_2NH$—, SONH—;
Y=O, S, NH; and
$A^1$, $A^2$, $B^1$, $B^2$, $C^1$, $C^2$ are independently chosen from H, $OR^4$, F.

Embodiments of the present invention also relate to pharmaceutically acceptable salts, solvates, or prodrugs of the compounds of formula II or IIA.

In some embodiments, $R^4$ is H or benzyl. In particular embodiments, the compound has the following structure:

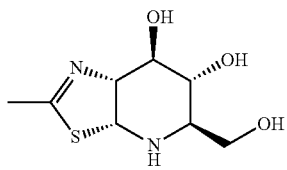

or is a pharmaceutically acceptable salt, solvate, or prodrug thereof.

Another aspect of the present invention pertains to a compound having a structure represented by formula III:

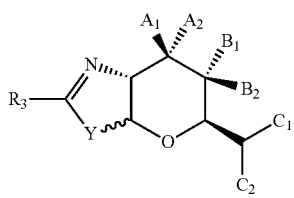

wherein: $R^3$, $R^4$ are independently chosen from H, $C_1$-$C_8$ alkyl, aryl, $(CH_2)_n$ aryl, $(CH_2)_n$ heteroaryl; n=0-8;
Y=O, S, NH; and
$A^1$, $A^2$, $B^1$, $B^2$, $C^1$, $C^2$ are independently chosen from H, $OR^4$, F.

In certain embodiments, the compound of formula III is not N-acetyl-glucosaminethiazoline.

Embodiments of the present invention also relate to pharmaceutically acceptable salts, solvates, or prodrugs of the compounds of formula III.

In some embodiments, $R^4$ is H or benzyl. In particular embodiments, the compound is selected from the group consisting of:

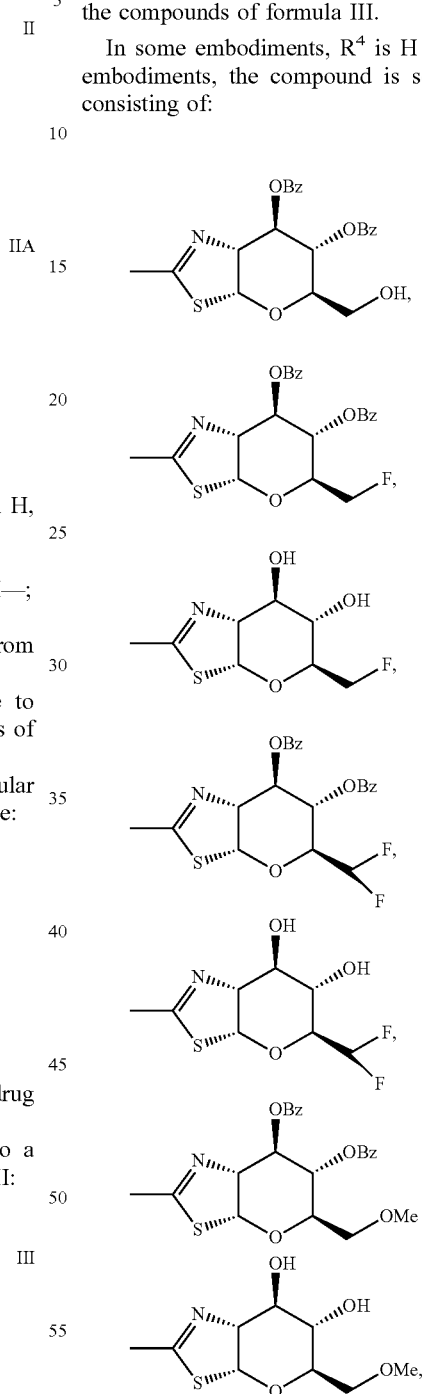

or a pharmaceutically acceptable salt, solvate, or prodrug thereof.

Synthesis

Another aspect of the invention pertains to methods of producing the above compounds. Scheme I below provides prophetic syntheses for exemplary compounds of formulae I and IA:

Scheme I
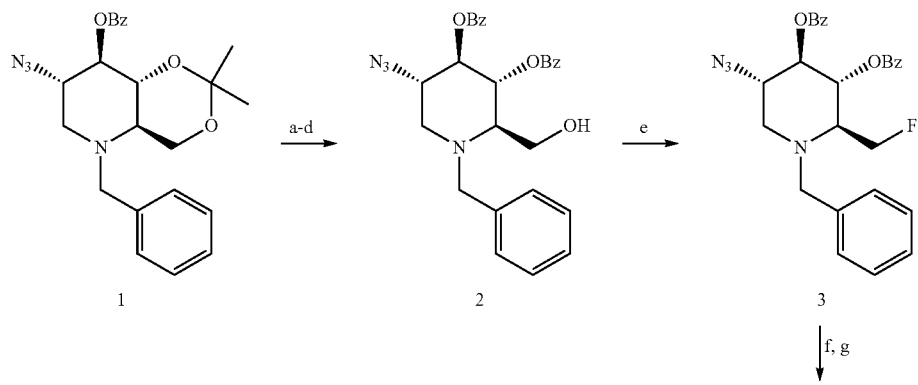
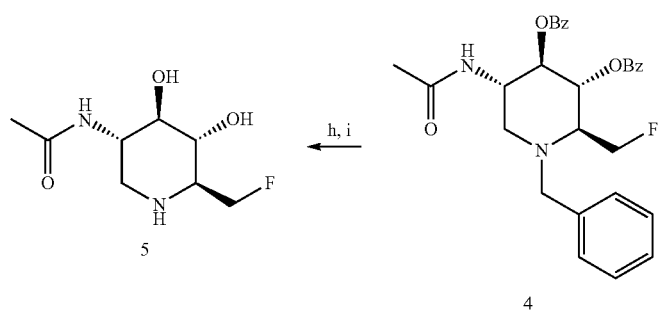
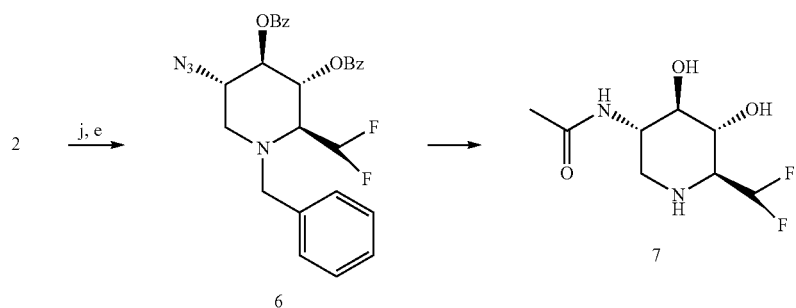
a) HCl, MeOH; b) TBDPSCl; c) BzCl, pyr; d) TBAF; e) DAST; f) H₂, RaNi; g) Ac₂O; h) NaOMe; H₂, Pd(OH)₂; j) [O]
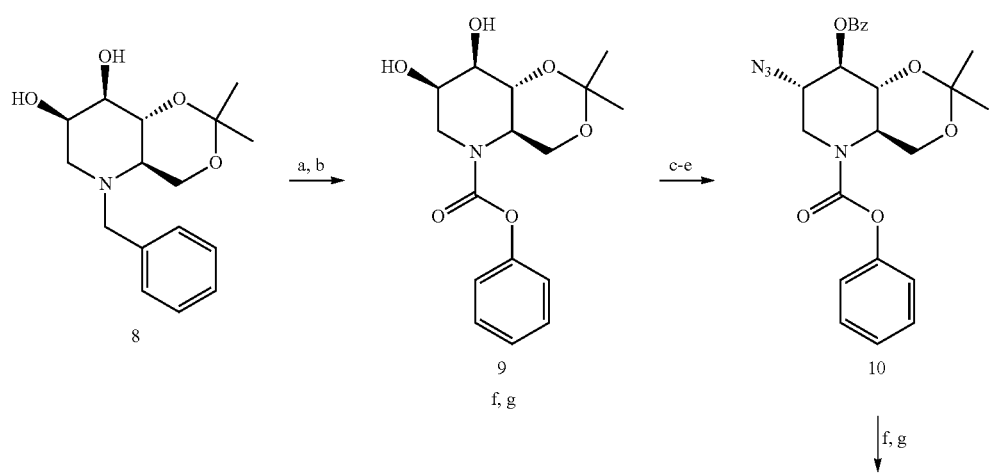

13                                                                    14

-continued

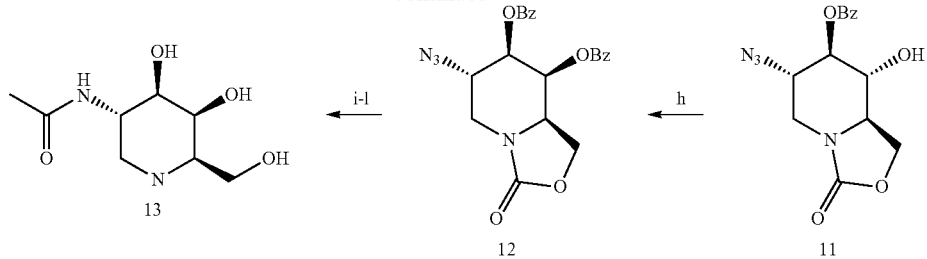

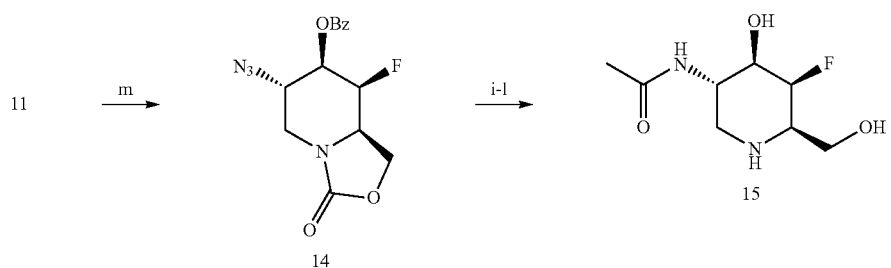

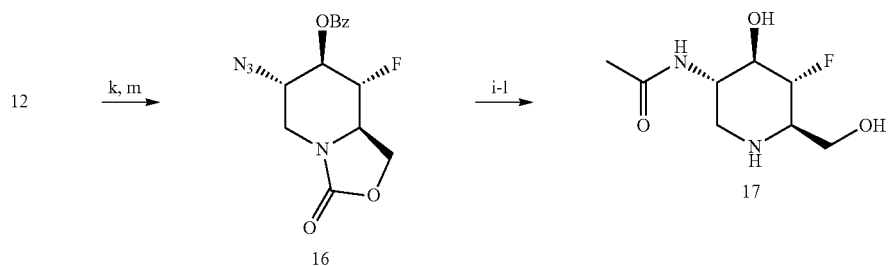

a) H$_2$, Pd(OH)$_2$; b) CbzCl; c) SOCl$_2$; d) NaN$_3$; e) BzCl; f) HCl, MeOH; g) K$_2$CO$_3$, DMF; h) Mitsuobu, PhCOOH; i) H$_2$, RaNi; j) Ac$_2$O; k) NaOMe; l) Ba(OH)2; m) DAST;

Based on the above Scheme I, one of ordinary skill in the art can produce the compounds according to formulae I and IA by selecting different appropriate starting compounds.

Scheme II below provides a prophetic synthesis for exemplary compounds of formulae II and IIA:

Scheme II

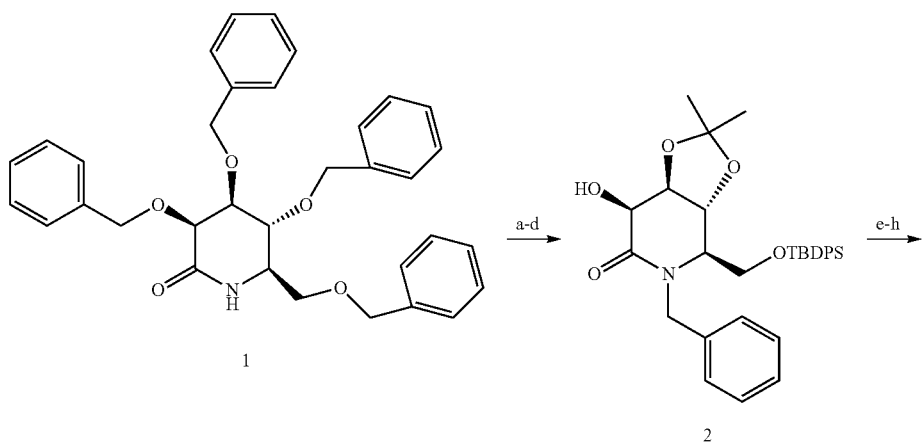

-continued

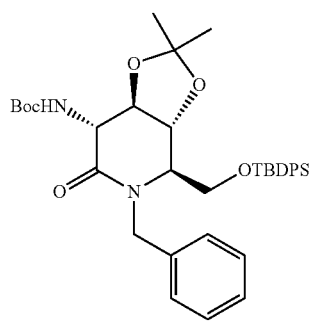

3

↓ i, j

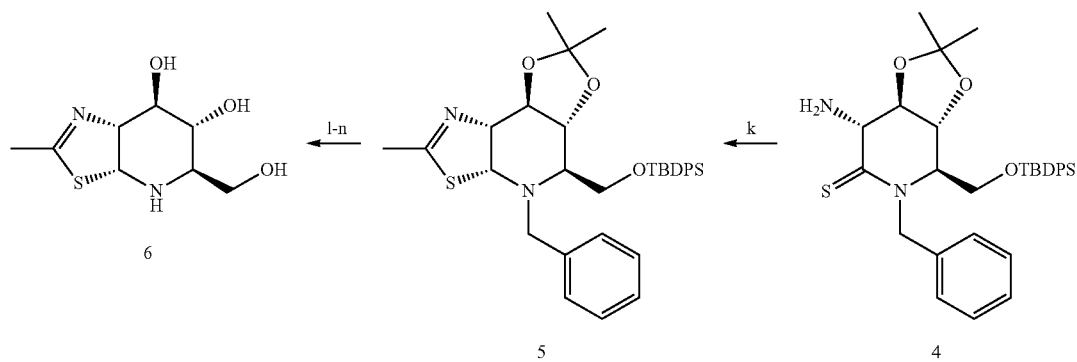

a) H₂, Pd(OH)₂; b) TBDPSCl; c) 2-methoxypropene H⁺; d) BnBr, K₂CO₃; e) MsCl, NEt₃; f) NaN₃; g) H₂, RaNi; h) Boc₂O; i) Lawesson's Rgt; j) TsOH; k) bromoacetone; l) HCl; m) TBAF; n) H₂, Pd(OH)₂

Based on the above Scheme II, one of ordinary skill in the art can produce the compounds according to formulae II and IIA by selecting different appropriate starting compounds.

Scheme III below provides prophetic syntheses for exemplary compounds of formula III:

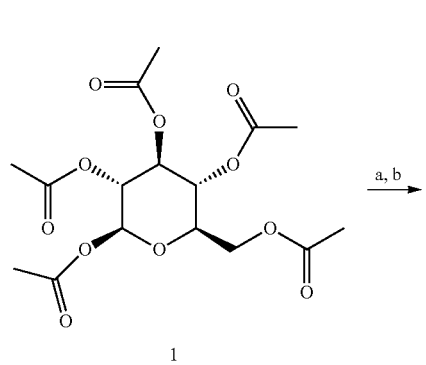

1

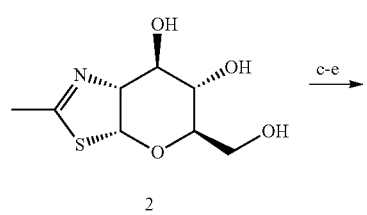

2

-continued

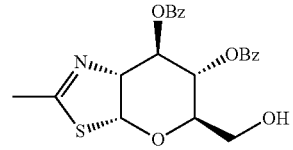

3

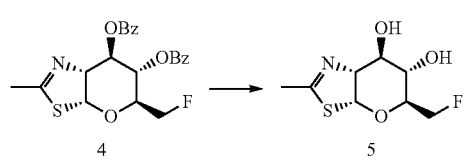

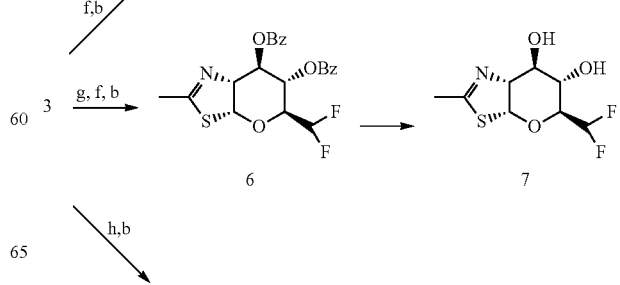

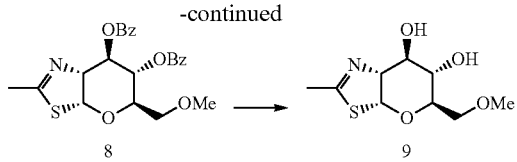

a) Lawesson's rgt; b) NaOMe; c) TBDPSCl; d) BzCl/pyr; e) TBAF; f), DAST; g) [O]; h) NaH/MeI Based on the above Scheme III, one of ordinary skill in the art can produce the compounds according to formula III by selecting different appropriate starting compounds.

Compositions/Formulations

Other aspects of the invention pertain to compositions/ formulations comprising any of the compounds described herein. Accordingly, one or more embodiments of the invention pertain to a pharmaceutical composition or formulation comprising: any of the compounds according to any of formulae I-III, or a pharmaceutically acceptable salt, solvate, or prodrug thereof; and at least one pharmaceutically acceptable carrier. The pharmaceutical composition may be prepared by adding a compound according to any of formulae I-III, or a pharmaceutically acceptable salt, solvate, or prodrug thereof to at least one pharmaceutically acceptable carrier.

Compounds of the present invention include pharmaceutically acceptable salts, solvates and pro-drugs of the compounds disclosed herein. Pharmaceutically acceptable salts include salts derived from inorganic bases such as Li, Na, K, Ca, Mg, Fe, Cu, Zn, Mn; salts of organic bases such as N,N'-diacetylethylenediamine, glucamine, triethylamine, choline, hydroxide, dicyclohexylamine, metformin, benzylamine, trialkylamine, thiamine; chiral bases like alkylphenylamine, glycinol, phenyl glycinol, salts of natural amino acids such as glycine, alanine, valine, leucine, isoleucine, norleucine, tyrosine, cystine, cysteine, methionine, proline, hydroxy proline, histidine, ornithine, lysine, arginine, serine; non-natural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, hydrochlorides, sulphates, nitrates, phosphates, perchlorates, borates, hydrohalides, acetates, tartrates, maleates, citrates, succinates, palmoates, methanesulphonates, benzoates, salicylates, benzenesulfonates, ascorbates, glycerophosphates, ketoglutarates. In one embodiment, the pharmaceutically acceptable salt of the compounds disclosed herein is the hydrochloride salt.

"Solvate" denotes a physical association of a compound with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. "Hydrate" is a solvate wherein the solvent molecule is $H_2O$. Other non-limiting examples of suitable solvates include alcohols (e.g., ethanolates, methanolates, and the like).

Prodrugs are compounds which are converted in vivo to active forms (see, e.g., R. B. Silverman, 1992, "The Organic Chemistry of Drug Design and Drug Action", Academic Press, Chapter 8, incorporated herein by reference). Additionally, a discussion of prodrugs is provided in T. Higuchi and V. Stella, Pro-drugs as Novel Delivery Systems, Volume 14 of the A.C.S. Symposium Series, and in Bioreversible Carriers in Drug Design, Edward B. Roche, ed., American Pharmaceutical Association and Pergamon Press, 1987, both of which are incorporated herein by reference thereto. Prodrugs can be used to alter the biodistribution (e.g., to allow compounds which would not typically enter the reactive site of the protease) or the pharmacokinetics for a particular compound. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound with a suitable derivatizing agent. For example hydroxy groups can be converted into esters via treatment with a carboxylic acid in the presence of a catalyst. Examples of cleavable alcohol prodrug moieties include substituted and unsubstituted, branched or unbranched lower alkyl ester moieties, (e.g., ethyl esters), lower alkenyl esters, di-lower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

The compounds of the present invention can be formulated to be suitable for any route of administration, including e.g., orally in the form of tablets or capsules or liquid, or in sterile aqueous solution for injection. When the compound is formulated for oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); or preservatives (e.g., methyl or propyl-p-hydroxybenzoates or sorbic acid). The liquid preparations may also contain buffer salts, flavoring, coloring or sweetening agents as appropriate. Preparations for oral administration may be suitably formulated to give controlled or sustained release of the compound.

In some embodiments, the route of administration is subcutaneous. Other routes of administration may be oral or parenteral, including intravenous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation In one or more embodiments of the present invention, the compound is administered in a dosage form that permits systemic distribution or uptake, such that the compound may cross the blood-brain barrier so as to exert effects on neuronal cells. Such dosage forms that permit systemic distribution or uptake may be oral or parenteral. In some embodiments, the compound may be distributed systemically, including crossing the blood-brain barrier.

For example, pharmaceutical formulations of the compound suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, polyethylene glycol, and the like), suitable mixtures thereof, or vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate or gelatin.

Sterile injectable solutions are prepared by incorporating the compound in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a commonly used excipient.

The formulation can also contain a non-ionic detergent. Examples of non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

Kits & Methods of Treatment

Other aspects of the invention pertain to compositions and kits comprising any of the compounds described herein. Accordingly, one or more embodiments of the invention pertain to a pharmaceutical composition or formulation comprising: any of the compounds according to any of formulae I-III, or a pharmaceutically acceptable salt, solvate, or prodrug thereof; and at least one pharmaceutically acceptable carrier.

Another aspect of the invention pertains to a kit comprising: a container having an effective amount of any of the compounds according to any of formulae I-III, or a pharmaceutically acceptable salt, solvate, or prodrug thereof, or any combination of two or more thereof; and instructions for using the same to prevent and/or treat Alzheimer's disease and/or CAA.

Yet another aspect of the invention pertains to a method of preventing and/or treating Alzheimer's disease and/or cerebral amyloid angiopathy, the method comprising administering to a patient in need thereof a therapeutically effective amount of any of the compounds discussed above. In some embodiments, the administration of an effective amount of the compound increases processing of one or more gangliosides selected from GM2 and GA2.

Yet another aspect of the present invention pertains to a method for enhancing the activity of β-hexosaminidase, the method comprising administering a therapeutically effective amount of any of the compounds discussed above.

The therapeutic agent(s) may be administered orally or parenterally, including intravenously, subcutaneously, intra-arterially, intraperitoneally, ophthalmically, intramuscularly, buccally, rectally, vaginally, intraorbitally, intracerebrally, intradermally, intracranially, intraspinally, intraventricularly, intrathecally, intracisternally, intracapsularly, intrapulmonarily, intranasally, transmucosally, transdermally, or via inhalation. In one preferred embodiment, the therapeutic agent(s) is administered orally.

Administration of therapeutic agent(s) may be by periodic injections of a bolus of the formulation, or may be administered by intravenous or intraperitoneal administration from a reservoir which is external (e.g., an i.v. bag) or internal (e.g., a bioerodable implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780, 014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Subcutaneous injections have the advantages allowing self-administration, while also resulting in a prolonged plasma half-life as compared to intravenous administration. Furthermore, a variety of devices designed for patient convenience, such as refillable injection pens and needle-less injection devices, may be used with the formulations of the present invention as discussed herein.

A suitable pharmaceutical preparation is in a unit dosage form. In such form, the preparation is subdivided into suitably sized unit doses containing appropriate quantities of the active component, e.g., an effective amount to achieve the desired purpose such as maximizing substrate clearance.

The amount of effective therapeutic agent(s) for preventing or treating the referenced disorder can be determined on a case-by-case basis by those skilled in the art, guided by the present specification and the examples herein. The amount and frequency of administration of the therapeutic agent(s) will be regulated according to the judgment of the attending clinician (physician) considering such factors as age, condition and size of the patient as well as risk for developing disorder or severity of the symptoms of the referenced disorder being treated.

The therapeutic agent(s) of the present invention can be administered in combination with at least one other therapeutic agent. Administration of the therapeutic agent(s) of the present invention with at least one other therapeutic agent is understood to encompass administration that is sequential or concurrent. In one embodiment, the therapeutic agents are administered in separate dosage forms. In another embodiment, two or more therapeutic agents are administered concurrently in the same dosage form.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A compound selected from the group consisting of:

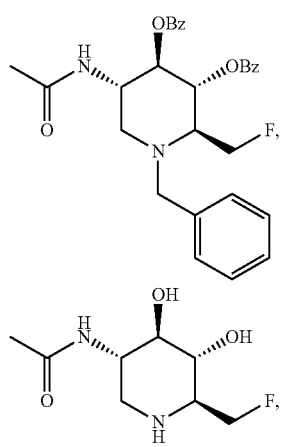

-continued

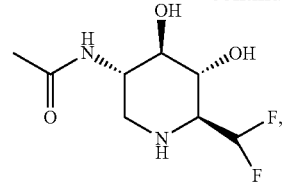

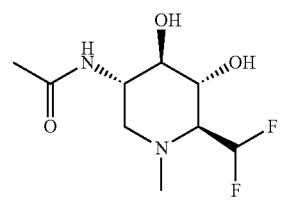

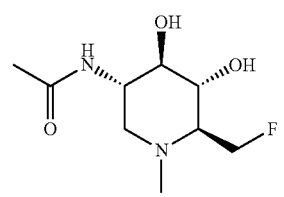

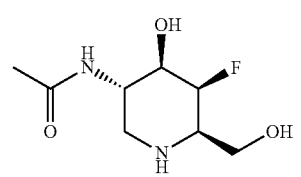

and

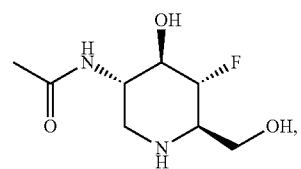

or a pharmaceutically acceptable salt or solvate thereof.

2. A pharmaceutical composition comprising:
   a. the compound of claim 1; and
   b. at least one pharmaceutically acceptable carrier.

3. A method for treating Alzheimer's disease and/or cerebral amyloid angiopathy in a patient diagnosed with the same, the method comprising administering to the patient an effective amount of the compound of claim 1.

4. The method of claim 3, wherein the administration of an effective amount of the compound increases processing of one or more gangliosides selected from GM2 and GA2.

5. A method for enhancing the activity of β-hexosaminidase, the method comprising administering an effective amount of the compound of claim 1.

6. A kit comprising:
   a. the compound of claim 1; and
   b. instructing for using the same to treat Alzheimer's disease and/or cerebral amyloid angiopathy.

7. The compound of claim 1, wherein the compound comprises:

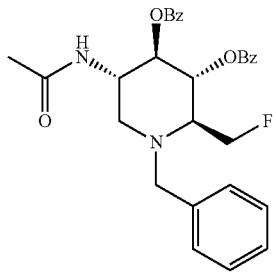

or a pharmaceutically acceptable salt or solvate thereof.

8. The compound of claim 1, wherein the compound comprises:

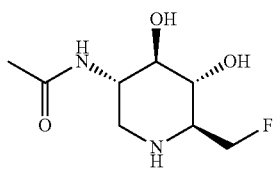

or a pharmaceutically acceptable salt or solvate thereof.

9. The compound of claim 1, wherein the compound comprises:

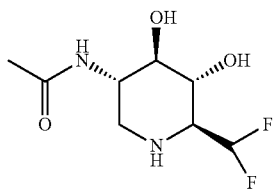

or a pharmaceutically acceptable salt or solvate thereof.

10. The compound of claim 1, wherein the compound comprises:

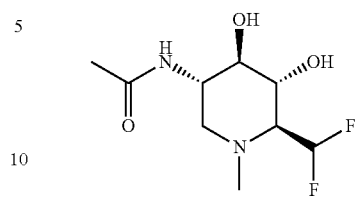

or a pharmaceutically acceptable salt or solvate thereof.

11. The compound of claim 1, wherein the compound comprises:

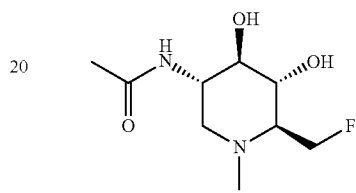

or a pharmaceutically acceptable salt or solvate thereof.

12. The compound of claim 1, wherein the compound comprises:

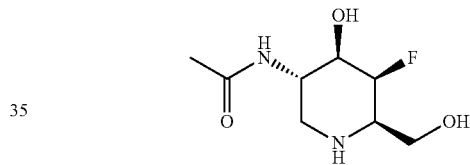

or a pharmaceutically acceptable salt or solvate thereof.

13. The compound of claim 1, wherein the compound comprises:

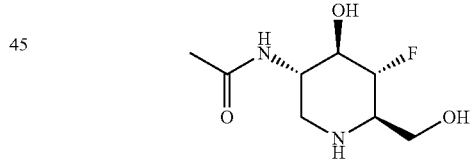

or a pharmaceutically acceptable salt or solvate thereof.

* * * * *